(12) United States Patent
Allen et al.

(10) Patent No.: US 10,098,721 B2
(45) Date of Patent: Oct. 16, 2018

(54) PELVIC IMPLANT NEEDLE SYSTEM AND METHOD

(75) Inventors: John J. Allen, Mendota Heights, MN (US); James R. Mujwid, Crystal, MN (US); Johannes N. Gaston, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 13/602,857

(22) Filed: Sep. 4, 2012

(65) Prior Publication Data

US 2013/0060080 A1    Mar. 7, 2013

Related U.S. Application Data

(60) Provisional application No. 61/530,380, filed on Sep. 1, 2011.

(51) Int. Cl.
| | |
|---|---|
| *A61F 2/04* | (2013.01) |
| *A61F 2/00* | (2006.01) |
| *A61B 17/34* | (2006.01) |
| *A61B 17/06* | (2006.01) |
| *A61B 17/00* | (2006.01) |

(52) U.S. Cl.
CPC ...... *A61F 2/0063* (2013.01); *A61B 17/06109* (2013.01); *A61B 17/3476* (2013.01); *A61F 2/0045* (2013.01); *A61B 2017/0042* (2013.01); *A61B 2017/0046* (2013.01); *A61B 2017/00805* (2013.01); *A61F 2002/0072* (2013.01)

(58) Field of Classification Search
CPC .............. A61B 17/062; A61B 17/0625; A61B 2017/00349; A61B 2017/0047; A61B 2017/0472; A61B 2017/06066; A61B 2017/06085; A61B 2017/00805; A61B 17/06109; A61B 2017/0042; A61B 2017/00424; A61B 2017/0046; A61F 2002/0072
USPC .............................................. 600/29, 30, 37
See application file for complete search history.

(56) References Cited

U.S. PATENT DOCUMENTS

| | | | |
|---|---|---|---|
| 2,738,790 | A | 3/1956 | Todt et al. |
| 3,124,136 | A | 3/1964 | Usher |
| 3,384,073 | A | 5/1968 | Van Winkle, Jr. |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

Aldridge, Albert, "Transplantation of Fascia for Relief of Urinary Stress Incontinence," Am. J. Obstetrics and Gynecology, V.44, pp. 398-411.

(Continued)

*Primary Examiner* — Thaddeus Cox
(74) *Attorney, Agent, or Firm* — Brake Hughes Bellermann LLP

(57) ABSTRACT

Various embodiments of a trocar or needle system for use in inserting and deploying pelvic implants are provided. The needle device can include a solid or hollow shaft portion with a non-circular cross-section. A grip element can be provided to slide along a length of the needle shaft to further facilitate handling.

20 Claims, 4 Drawing Sheets

(56) References Cited

U.S. PATENT DOCUMENTS

| | | |
|---|---|---|
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 4,019,499 A | 4/1977 | Fitzgerald |
| 4,172,458 A | 10/1979 | Pereyra |
| 4,246,660 A | 1/1981 | Wevers |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,036,867 A | 8/1991 | Biswas |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,386,836 A | 2/1995 | Biswas |
| 5,413,598 A | 5/1995 | Moreland |
| 5,474,518 A | 12/1995 | Velaquez |
| 5,474,543 A | 12/1995 | McKay |
| 5,518,504 A | 5/1996 | Polyak |
| 5,520,700 A | 5/1996 | Beyar et al. |
| 5,527,342 A | 6/1996 | Pietrzak et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,643,320 A | 7/1997 | Lower et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,934,283 A | 8/1999 | Willem et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van de Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |

(56) References Cited

U.S. PATENT DOCUMENTS

| | | |
|---|---|---|
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Bryon et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,762,942 B2 | 7/2010 | Neisz et al. |
| 7,766,926 B2 | 8/2010 | Bosely et al. |
| 7,789,821 B2 | 9/2010 | Browning |
| 7,927,342 B2 | 4/2011 | Rioux |
| 7,981,024 B2 | 7/2011 | Levy |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0010929 A1 | 1/2003 | Prieve et al. |
| 2003/0036676 A1 | 2/2003 | Scetbon |
| 2003/0065402 A1 | 4/2003 | Anderson et al. |
| 2003/0176875 A1* | 9/2003 | Anderson et al. ........... 606/151 |
| 2004/0015057 A1 | 1/2004 | Rocheleau et al. |
| 2004/0073235 A1 | 4/2004 | Lund |
| 2004/0098048 A1 | 5/2004 | Cunningham et al. |
| 2004/0144395 A1* | 7/2004 | Evans ............... A61B 17/06066 128/885 |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015001 A1* | 1/2006 | Staskin et al. ................ 600/30 |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2008/0140218 A1 | 6/2008 | Staskin et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0112258 A1 | 4/2009 | Kreidler et al. |
| 2009/0221868 A1 | 9/2009 | Evans |
| 2010/0022822 A1 | 1/2010 | Walshe |
| 2010/0217069 A1* | 8/2010 | Meade ............... A61B 17/0485 600/37 |
| 2010/0261950 A1 | 10/2010 | Lund |
| 2011/0124954 A1 | 5/2011 | Odhahl |
| 2011/0124956 A1* | 5/2011 | Mujwid ............... A61F 2/0045 600/30 |
| 2011/0270281 A1 | 11/2011 | Malkowski et al. |
| 2012/0016185 A1 | 1/2012 | Sherts et al. |
| 2012/0065461 A1 | 3/2012 | Chu et al. |

FOREIGN PATENT DOCUMENTS

| | | |
|---|---|---|
| DE | 4220283 C2 | 5/1994 |
| DE | 19544162 | 4/1997 |
| DE | 10211360 | 9/2003 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |

(56) References Cited

FOREIGN PATENT DOCUMENTS

| | | |
|---|---|---|
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

Amundsen et al., "Anatomical correction of vaginal vault prolapse by uterosacral ligament fixation in women who also require a pubovaginal sling," The J. of Urology, vol. 169, 1770-1776, May 2003.

Araki, Tohru, et. al., "The Loop-Loosening Procedure for Urination Difficulties After Stamey Suspension of the Vesical Neck," J. of Urology, vol. 144, Aug. 1990, pp. 319-323.

Asmussen et. al., "Simultaneous Urethro-Cystometry with a New Technique," Scand. J. Urol. Nephrol 10:7-11, 1976, pp. 7-10.

Beck et. al., "Treatment of Urinary Stress Incontinence with Anterior Colporrhapy," J. of Am. Col. of Obstetricians and Gynecologists, V.59, No. 3, Mar. 1982, pp. 269-274.

Benderev, Theodore, "A Modified Percutaneous Outpatient Bladder Neck Suspension System," The J. of Urology, vol. 152, Dec. 1994, pp. 2316-2320.

Benderev, Theodore, "Anchor Fixation and Other Modifications of Endoscopic Bladder Neck Suspension," Urology, vol. 40, No. 5, Nov. 1992, pp. 409-419.

Bergman, et. al., "Three Surgical Procedures for Genuine Stress Incontinence: Five-Year Follow-up of a Prospective Randomized Study," Am. J. Obstetrics and Gynecology, vol. 173, No. 1, pp. 66-71.

Blaivas et. al., "Pubovaginal Fascial Sling for the Treatment of Complicated Stress Urinary Incontinence," The J. of Urology, vol. 145, Jun. 1991, pp. 1214-1218.

Blaivas et. al., "Commentary: Pubovaginal Sling Procedure," Surgery for Female Urinary Incontinence, pp. 93-102.

Blaivas et. al., "Type III Stress Urinary Incontinence: Importance of Proper Diagnosis and Treatment," Gynecology and Obstetrics, pp. 473-476.

Boston Scientific, "Advantage A/T Surgical Mesh Sling Kits," 6 pages.

Bryans et. al. "Marlex Gauze Hammock Sling Operation with Cooper's Ligament Attachment in the Management of Recurrent Urinary Stress Incontinence," Am. J. Obstetrics and Gynecology, vol. 133, Issue 3, Feb. 1979, pp. 292-294.

Burch, John C., "Urethrovaginal fixation to Cooper's ligament for correction of stress incontinence, cystocele, and prolapse," Am. J. Obstetrics and Gynecology, vol. 31, No. 2, Feb. 1961.

Cervigni et al., "The use of synthetics in the treatment of pelvic organ prolapse," Current Opinion in Urology 2011, 11:429-435.

Conquy, Dophle, "Le point sur L'incontinence urinaire," Expertise et practiques en urologie, No. 3, 1998.

Das et al., "Laparoscopic colpo-suspension," J. of Urology, vol. 154, pp. 1119-1121, Sep. 1995.

DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.

Eglin et al., Transobturator subvesical mesh: tolerance and short-term results of a 103 case continuous series, Service de gynecologic clinque Dhampeau 32 (Nov. 2002).

Enzelsberger et al., "Urodynamic and radiologic parameters before and after loop surgery for recurrent urinary stress incontinence," Acta. Obstet. Gynecol. Scand., 1990; 69:51-54.

Eriksen et al., "Long-term effectiveness of the Burch colposuspension in female urinary stress incontinence," Acta. Obstet. Gynecol. Scand., 1990; 69:45-50.

Falconer et al., "Clinical outcome and changes in connective tissue metabolism after intravaginal slingplasty in stress incontinent women," Int. Urogynecol. J. (1996) 7:133-137.

(56) References Cited

OTHER PUBLICATIONS

Farnsworth, B. N., "Posterior intravaginal slingplasty (infracoccygeal sacropexy) for severe posthysterectomy and vaginal vault prolapse—a preliminary report on efficacy and safety," Int. Urogynecol J (2002) 13:4-8.
Gilja et al., "A modifies raz bladder neck suspension operation (transvaginal burch)," The J. of Urology, vol. 153, 1455-1457, May 1995.
Gittes et al., "No-incision pubovaginal suspension for stress incontinence," The J. of Urology, vol. 138 (1987), pp. 568-570.
Gynecare TVT, "The tension-free solution to female incontinence," ICS/IUGA Symp. 2002.
Hamilton et al., "Procedures for urinary incontinence in the United States, 1979-1997," Am. J. Obstet. Gynecol. vol. 189, No. 1, pp. 70-75 2003.
Handa et al., "Banked Human fascia lata for the suburethral sling procedure: a preliminary report," Obstetrics & Gynecology, vol. 88, No. 6, pp. 1045-1050, Dec. 1996.
Henriksson et al., "A urodynamic evaluation of the effects of abdominal urethrocystopexy and vaginal sling urethroplasty in women with stress incontinence," Am. J. Obstet. Gynecol., vol. 131, No. 1, pp. 77-83, May 1978.
Hodgkinson et al., "Urinary stress incontinence in the female: III. Round-ligament technic for retropubic suspension of the urethra," Obstetrics & Gynecology, vol. 10, No. 5 (1957).
Holschneider et al., "The modified pereyra procedure in recurrent stress urinary incontinence: a 15 year review," Obstetrics & Gynecology, vol. 83, No. 4 pp. 573-579 (1994).
Ingelman-Sundberg, "Surgical treatment of female urinary stress incontinence," Contr. Gynec. Obstet., vol. 10 pp. 51-69 (1983).
Klutke et al., "The anatomy of stress incontinence: magnetic resonance imaging of the female bladder neck and urethra," The J. or Urology, vol. 149, pp. 563-567 (1990).
Klutke et al., "Instruments & Methods: transvaginal bladder neck suspension to cooper's ligament: a modified pereyra procedure," Obstetrics & Gynecology, vol. 88, No. 2, pp. 293-297 (1996).
Leach et al., "Female stress urinary incontinence clinical guidelines panel summary report on surgical management of female stress urinary incontinence," Am. Urological Assc., vol. 158, 875-880 (1997).
Loughlin et al., "Review of an 8-year experience with modifications of endoscopic suspension of the bladder neck for female stress urinary incontinence," The Journal of Urology, vol. 143, pp. 3-4 (1990).
Marshall et al., "The correction of stress incontinence by simple vesicourethral suspension," pp. 509-514.
McGuire, Edward, "Abdominal procedure for stress incontinence," Urologic Clinics of North America, vol. 12 No. 5, pp. 285-291 (1985).
McKiel et al., "Marshall-Marchetti procedure: modifications," The Journal of Urology, vol. 96 (1966).
Mascio, Valenzio, "Therapy of urinary stress incontinence in women using Mitek GII Anchors," Mitek Surgical Brochure.
O'Donnell, Pat, "Combined Raz urethral suspension and McGuire pubovaginal sling for treatment of complicated stress urinary incontinence," The J. of the Ark. Med. Society, vol. 88, No. 8, pp. 389-392 (1992).
Parra et al., "Experience with a simplified technique for the treatment of female stress urinary incontinence," British J. of Urology, vol. 68:615-617 (1990).
Pereyra, Armand, "A simplified surgical procedure for the correction of stress incontinence in women," West. J. Obst. & Gynec., Jul./Aug. (1959).
Pereyra, Armand, "Pubourethral supports in perspective: modified pereyra procedure of urinary incontinence," Obstet. & Gyne. vol. 59. No. 5 (1992).
Petros et al., "The autogenic ligament procedure: a technique for planned formation of an artificial neo-ligament," Acta Obstet Gynecol Scand, 69 Suppl. 153:43-51 (1990).

Petros et al., "Cough transmission ratio: an indicator of suburethral vaginal wall tension rather than urethral closure?", Acta Obstet Gynecol Scand, 69 Suppl. 153:43-51 (1990).
Petros et al., "Cure of stress incontinence by repair of external anal sphincter," Acta Obstet Gynecol Scand, 69 Suppl. 153:75 (1990).
Petros et al., "Non stress non urge female urinary incontinence—diagnosis and cure: a preliminary report," Acta Obstet Gynecol Scand, 69 Suppl. 153:69-70 (1990).
Petros et al., "The role of a lax posterior vaginal fornix in the causation of stress and urgency symptoms: a preliminary report," Acta Obstet Gynecol Scand, 69 Suppl. 153:71-73 (1990).
Petros et al., "The tethered vagina syndrome, post surgical incontinence and I-plasty operation for sure," Acta Obstet Gynecol Scand, 69 Suppl. 153:63-67 (1990).
Petros et al., "Bladder instability in women: a premature activation of the micturition reflex," Neurourology and Urodynamics, 12:235-239 (1993).
Petros et al., "Urethral pressure increase on effort originates from within the urethra, and continence from musculovaginal closure," Neurourology and Urodynamics, 14:337-350 (1995).
Petros et al., "An analysis of rapid pad testing and the history for the diagnosis of stress incontinence," Acta Obstet Gynecol Scand, 71:529-536 (1992).
Petros et al., "An integral theory of female urinary incontinence," Acta Obstet Gynecol Scand, 69 Suppl. 153:7-31 (1990).
Petros et al., "The tuck procedure: a simplified vaginal repair for treatment of female urinary incontinence," Acta Obstet Gynecol Scand, 69 Suppl. 153:41-42 (1990).
Petros et al., "Anchoring the midurethra restores bladder-neck anatomy and continence," The Lancet, vol. 354 (1999).
Petros et al., "The development of the intravaginal slingplasty procedure: IVS II (with bilateral tucks)," Scand. J. Urol. Nephrol. Suppl. No. 153:61-69 (1993).
Petros et al., "Part IV: Surgical applications of the theory—Development of the intravaginal sling plasty (IVS) procedure," Scand. J. Urol. Nephrol. Suppl. No. 153:53-57 (1993).
Petros et al., "The free graft procedure for the cure of the tethered vagina syndrome," Scand. J. Urol. Nephrol. Suppl. No. 153:85-89 (1993).
Petros et al., "An anatomical basis for success and failure of female incontinence surgery," Scand. J. Urol. Nephrol. Suppl. No. 153:55-61 (1993).
Petros et al., "Part II. The biomechanics of vaginal tissue and supporting ligaments with special relevance to the pathogenesis of female urinary incontinence," Scand. J. Urol. Nephrol. Suppl. No. 153:29-31 (1993).
Petros et al., "The further development of the intravaginal slingplasty procedure: IVS IV—(with double-brested unattached vaginal flap repair and free vaginal tapes)," Scand. J. Urol. Nephrol. Suppl. No. 153:73-80 (1993).
Petros et al., "The further development of the intravaginal slingplasty procedure: IVS V—(with double-brested unattached vaginal flap repair and free vaginal tapes)," Scand. J. Urol. Nephrol. Suppl. No. 153:77-81 (1993).
Petros et al., "Further development of the intravaginal slingplasty procedure—IVS III (with midline tuck)," Scand. J. Urol. Nephrol. Suppl. No. 153:69-73 (1993).
Petros et al., "Medium term follow-up of the intravaginal slingplasty operation indicates minimal deterioration of urinary continence with time."
Petros et al., "New ambulatory surgical methods using an anatomical classification of urinary dysfunction improve stress, urge and abnormal emptying," Urogynecology Journal.
Petros et al., "Pelvic floor rehabilitation according to the integrated theory of female urinary incontinence," Pelvic Floor Dysfunction—investigations & conservative treatment.
Petros et al., "Part III. Surgical principles deriving from the theory," Scand. J. Urol. Nephrol. Suppl. No. 153:41-53 (1993).
Petros et al., "Part I. Theoretical, morphological, radiological correlations and clinical perspective," Scand. J. Urol. Nephrol. Suppl. No. 153:5-29 (1993).
Raz et al., "The Raz bladder neck suspension: results in 206 patients," The Journal of Urology, pp. 845-846 (1992).

(56) References Cited

OTHER PUBLICATIONS

Raz et al., "Modified bladder neck suspension for female stress incontinence," Urology, vol. XVII, No. 1, pp. 82-86 (1981).
Richardson et al., "Delayed reaction to the Dacron buttress used in urethropexy," vol. 29, No. 9, pp. 690-694 (1984).
Roberts, Henry, "Cystourethrography in Women," Cystourethrography in Women, vol. XXV No. 293, pp. 253-260 (1952).
Seim et al., "A study of female urinary incontinence in general practice," Scand. J. Urol. Nephrol 30;465-471 (1996).
Sloan et al., "Stress incontinence of urine: a retrospective study of the complications and late results of simple suprapubic suburethral fascial slings," The Journal of Urology, vol. 110, pp. 533-537 (1953).
Spencer et al., "A comparison of endoscopic suspension of the vesical neck with suprapubic vesicourethropexy for treatment of stress urinary incontinence," The Journal of Urology, vol. 137, pp. 411-416 (1987).
Stamey, Thomas, "Endoscopic suspension of the vesical neck for urinary incontinence in females," Am. Surg. pp. 465-472 (1980).
Stanton, Stuart, "Suprapubic approaches for stress incontinence in women," JAGS 38;348-351 (1990).
Stanton et al., "Surgery of female incontinence," ch. 7, pp. 105-115.
Studdiford, William, "Transplantation of abdominal fascia for the relief of urinary stress incontinence," Am. J. Obst & Gyne. vol. 47, pp. 764-776 (1994).
Tyco Heathcare, "IVS Tunneller," ICS/IUGA Symp. (2002).
Tyco Heathcare, "IVS Tunneller," ICS/IUGA Symp. (2001).
Ulmsten et al., "The unstable female urethra," Am. J. Obstet & Gynecol. vol. 144, No. 1 (1982).
Ulmsten et al., "Different biochemical composition of connective tissue in continent and stress incontinent women," Acta Obstet. Gynecol. Scand. 66:455-457 (1987).
Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).
Ulmsten et al., "An ambulatory surgical procedure under local anesthesia for treatment of female urinary incontinence," Int. Urogynecology J. 7:81-86 (1996).
Ulmsten et al., "A multicenter study of tension-free vaginal tape (TVT) for surgical treatment of stress urinary incontinence," Int. Urogynecology J. 9:210-213 (1998).
Ulmsten et al., "A three-year follow up of tension free vaginal tape for surgical treatment of female stress urinary incontinence," British Journal of Obstetrics and Gynaecology, vol. 106 pp. 345-350 (1999).
Waxman et al., "Advanced urologic surgery for urinary incontinence," The female Patient, vol. 21, pp. 93-101 (1996).
Webster et al., "Voiding dysfunction following cystourethropexy: its evaluation and management," The Journal of Urology vol. 144, pp. 670-674 (1990).
Webster, George, "Female Urinary Incontinence," Urologic Surgery, 3$^{rd}$ Ed., pp. 665-680 (1983).
Winter, Chester, "Peripubic urethropexy for urinary stress incontinence in women," Urology, vol. XX No. 4, pp. 408-412 (1982).
Woodside et al., "Suprapubic endoscopic vesical neck suspension for the management of urinary incontinence in myelodysplastic girls," The Journal of Urology vol. 135, pp. 97-101 (1986).
Zacharin, Robert, "The suspensory mechanism of the female urethra," Journal of Anatomy, vol. 97, Part 3, pp. 423-430 (1963).
Zimmern et al., "Four-Corner bladder neck suspension," Vaginal Surgery for the Urologist, vol. 2, No. 1 pp. 29-37 (1994).
Heit et al., "Predicting treatment choice for patients with pelvic organ prolapse," The Am. College of Obstet. & Gyn., vol. 101, No. 6, Jun. 2003.
Julian, Thomas, "The efficacy of Marlex mesh in the repair of severe, recurrent vaginal prolapse of the anterior midvaginal wall," Am. J. Obstet. Gynecol. vol. 175, No. 6, pp. 1471-1476 (1996).
Karram et al., "Surgical Treatment of Vaginal Vault Prolapse," Urogynecology and reconstructive pelvic surgery, Mosby (1999).
Luber, et al., "The demographics of pelvic floor disorders: current observations and future projections," Am. J. Obstet. Gynecol. vol. 184, No. 7, pp. 1496-1504 (2001).
Mage, PH., "L-interposition d'un treillis synthetique dans la cure par voie vaginale des prolapses genitaux," Technique chirurgicale, J. Gynecol. Obstet. Reprod. 1999:28:825-829.
Marchionni, et al., "True incidence of vaginal vault prolapse: thirteen years of experience," J. of Reproductive Medicine, vol. 44, No. 8, pp. 679-685 (1999).
Migliari et al., "Tension-free vaginal mesh repair for anterior vaginal wall prolapse," Eur. Urol. 2000;38:151-155.
Morley et al., "Sacrospinous ligament fixation for eversion of the vagina," Am. J. Obstet. Gynecol., vol. 158, No. 4, pp. 871-881 (1988).
Morley, Patrick, "Vaginal reconstruction of a complete vaginal prolapse: the transobturator repair," Journal of Urology, vol. 169 (4) supplement, p. 183 (2003).
Nicita, Giulio, "A new operation for genitourinary prolapse," The Journal of Urology, vol. 160, 741-745 (1998).
Paraiso, et al., "Laparoscopic surgery for enterocele, vaginal apex prolapse and rectocele," Int. Urogynecol. J. 10:223-239 (1990).
Paraiso, et al., "Pelvic support defects and visceral and sexual function in women treated with sacrospinous ligament suspension and pelvic reconstruction," Am. J. Obstet. & Gyne. vol. 175, No. 6 (1996).
Petros, P.E., "Vault Prolapse II: restoration of dynamic vaginal supports by infracoccygeal sacropexy, and axial day-case vaginal procedure," Int. Urogynecol. J. (2001) 12:296-303.
Petros, et al., "The posterior fornix syndrome: a multiple symptom complex of pelvic pain and abnormal urinary symptoms deriving from laxity in the posterior fornix of vagina," Scand. J. Urol. Nephrol. Suppl. No. 153, pp. 89-95 (1993).
Richter, Kurt, "Massive eversion of the vagina: pathogenesis, diagnosis, and therapy of the 'true' prolapse of the vaginal stump," Clinical Obstet. & Gyne., vol. 25, No. 4, pp. 897-911 (1982).
Sanz et al., "Modification of abdominal sacrocolpopexy using a suture anchor system," Journal of Reproductive Medicine, vol. 48, No. 7, pp. 496-501 (2003).
Subak et al., "Cost of pelvic organ prolapse surgery in the United States," Am. College Obstet. & Gyne., vol. 98, No. 4, pp. 464-452 (2001).
Sullivan et al., "Total pelvic mesh repair," Dis Colon Rectum, vol. 44, No. 6 pp. 857-864 (2001).
Swift et al., "Case-control study of etiologic factors in the development of severe pelvic organ prolapse," Int. Urogynecol. J. 12:187-192 (2001).
Visco et al., "Vaginal mesh erosion after abdominal sacral colpopexy," Am. J. Obstet. Gynecol. vol. 184, No. 3, pp. 297-303 (2001).
Weber et al., "Anterior vaginal prolapse review of anatomy and techniques or surgical repair," Obstet. & Gyne., vol. 89, No. 2, pp. 310-318 (1997).
Winters et al., "Abdominal sacral colpopexy and abdominals enterocele repair in the management of vaginal vault prolapse," Urology 56 (Suppl. 6A) pp. 56-64(2000).

\* cited by examiner

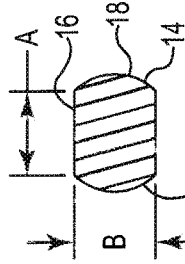
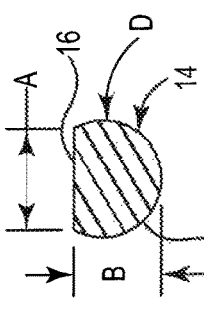
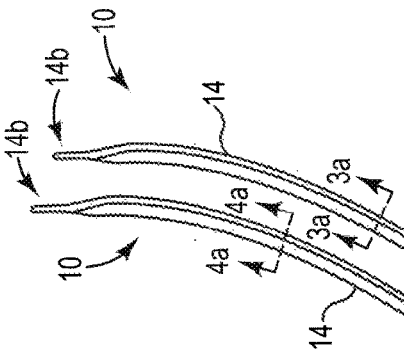
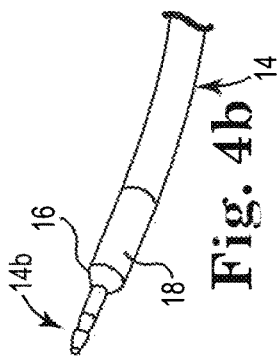
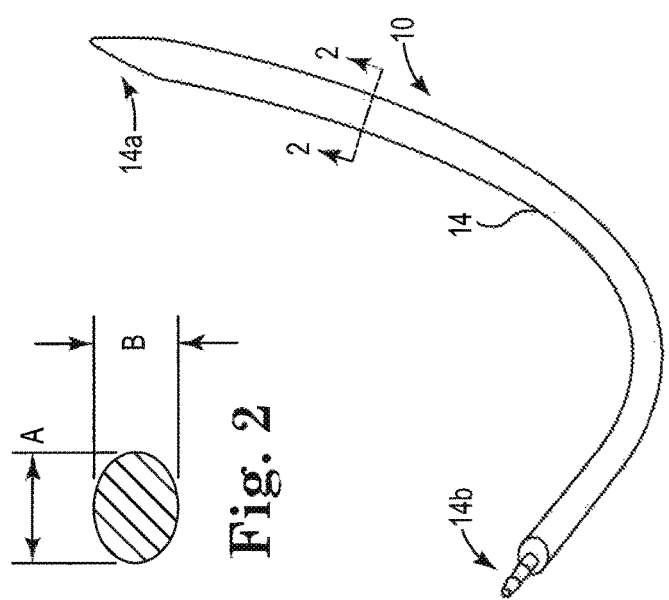
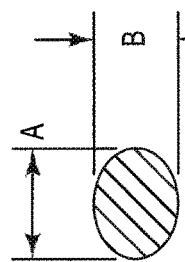

PELVIC IMPLANT NEEDLE SYSTEM AND METHOD

PRIORITY

This Application claims priority to and the benefit of U.S. Provisional Patent Application No. 61/530,380, filed Sep. 1, 2011, which is incorporated herein by reference in its entirety.

FIELD OF THE INVENTION

The present invention relates generally to surgical methods and apparatus and, more specifically, to surgical trocar or needle devices used for introducing and deploying an implant or sling to treat incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implant and introduction system that can be used to treat incontinence, and/or pelvic organ prolapse and other conditions.

SUMMARY OF THE INVENTION

The present invention describes an implant or sling insertion needle or trocar system, device and method. While typical trocars can include a curved stainless steel needle to create a pathway for a supporting mesh sling, embodiments of the present needle device can include a solid or hollow needle shaft portion with a non-circular cross-section. The use of a non-circular form for the needle provides distinct functional advantages.

Namely, a needle device having a non-circular cross-section needle shaft can provide improved visual and tactile feedback pertaining to the orientation of the needle, better gripping control of the needle, and improved finger contact surfaces to reduce finger pressure and slippage.

Embodiments can include a needle device having a housing or grip element. The grip can be constructed of a rigid plastic material, suitably shaped for gripping by the physician's fingers. The grip element can include flats, curved portions, holes, a through-aperture or other constraining means by which it may be slidably attached to the needle. In certain embodiments, for instance, the through-aperture is shaped and sized to generally match the shape and size of the needle, e.g., non-circular cross-section. As such, the grip element can slide along a longitudinal length of the non-circular cross-section needle, while still restricting rotational movement about the needle shaft. A mechanism can be included with the element, e.g., button or actuator, to selectively stop sliding of the element along the needle when desired. The mechanism allows the physician to apply both axial and rotational loads on the needle.

The needles described and depicted herein can be employed in treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Implants utilized with the system can include a tissue support portion and one or more anchors, arms and the like.

Embodiments of the present invention may be incorporated into or provided with various commercial products marketed by American Medical Systems of Minnetonka, Minn., as the MiniArc® Single-Incision Sling and like implant or anchoring systems.

BRIEF DESCRIPTION OF THE DRAWINGS

FIG. 1 is a schematic view of a non-circular, generally elliptical, needle device, in accordance with embodiments of the present invention.

FIG. 2 is a schematic cross-sectional view of the non-circular, generally elliptical, needle device of FIG. 1, in accordance with embodiments of the present invention.

FIG. 3 is a schematic view of a non-circular needle device, with flat and curved portions, in accordance with embodiments of the present invention.

FIG. 3a is a schematic cross-sectional view of the non-circular needle device of FIG. 3, in accordance with embodiments of the present invention.

FIG. 3b is a partial schematic view of a non-circular needle device, with flat and curved portions, in accordance with embodiments of the present invention.

FIG. 4 is a schematic view of a non-circular needle device, with flat and curved portions, in accordance with embodiments of the present invention.

FIG. 4a is a schematic cross-sectional view of the non-circular needle device of FIG. 4, in accordance with embodiments of the present invention.

FIG. 4b is a partial schematic view of a non-circular needle device, with flat and curved portions, in accordance with embodiments of the present invention.

DETAILED DESCRIPTION OF PREFERRED EMBODIMENTS

Figure 5:
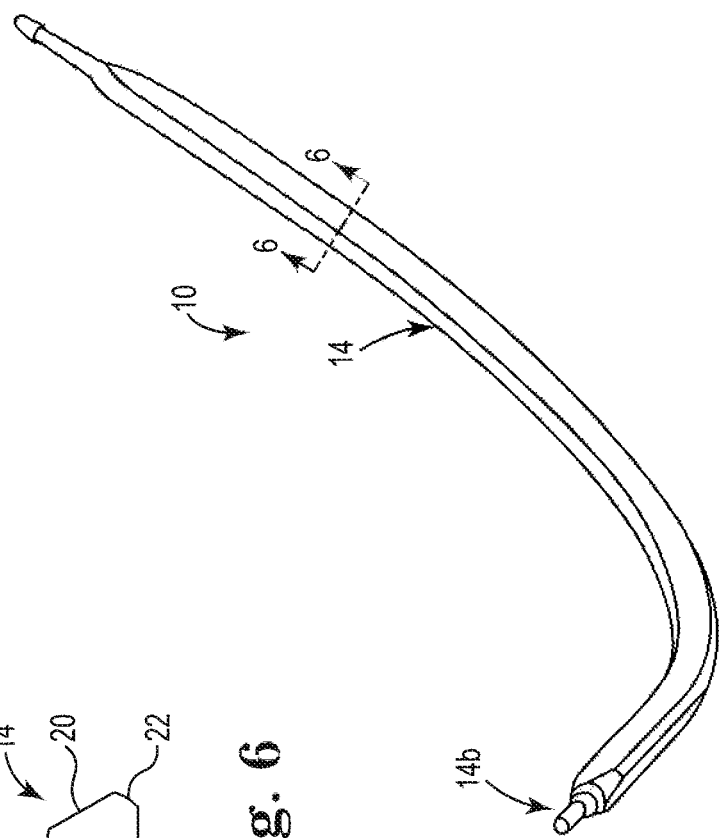
FIG. 5 is a schematic view of a non-circular trilobe needle device, in accordance with embodiments of the present invention.

Referring generally to FIGS. 1-10, various embodiments of a trocar or needle device 10 are shown. The needle device 10 described and depicted herein can be employed in introducing or deploying implants used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Implants utilized with the system can include a tissue support portion and one or more anchors, arms and the like, as disclosed herein.

The needle devices 10 can include a handle portion 12 and a needle portion 14. The needle portion 14 can be curved, straight, helical, and the like. The needle portion 14 can include a proximal portion 14a and a distal tip portion 14b. The proximal portion 14a can be operatively connected to the handle portion 12.

The needle 14 of the present invention can include a solid or hollow shaft with a non-circular cross-section. The use of a non-circular form for the needle 14 provides distinct functional advantages. Namely, a non-circular cross-section needle 14 provides improved visual and tactile feedback pertaining to the orientation of the needle, better gripping control of the needle, and improved finger contact surfaces to reduce finger pressure and slippage. In addition, defined flat or angular surfaces along portions of the needle 14 shaft can provide a desirable construct to restrict rotation of any device or mechanism adapted to slide along a length of the needle 14.

Referring generally to FIGS. 1-6, the non-circular form of the needle 14 can take on numerous shapes and configurations. For instance, in one embodiment, the cross-section can be generally elliptical, as shown in FIGS. 1-2. Such a generally elliptical structure can be defined by a horizontal dimension A and a vertical dimension B. In certain embodiments, dimension A can be defined in a range of approximately 0.150 inches to 0.200 inches, with dimension B defined in a range of approximately 0.100 inches and 0.150 inches. Other dimensional characteristics can be employed with various embodiments without deviating from the spirit and scope of the present invention.

As shown in FIGS. 3-4b, embodiments of the needle 14 can include one or more flat portions 16 and one or more curved portions 18 to define the non-circular needle cross-section. The one or more curved portions 18 can be generally concave, convex, or a combination thereof. The one or more flat portions 16 can facilitate and promote contact and stability for the physician's finger to provide orientation feedback and granular control. The flat portions 16 can face either toward the inside or outside of the needle bend, for those embodiments having a curved needle 14. The horizontal portion A can be defined in a range of approximately 0.150 inches to 0.175 inches, with the vertical dimension B defined in a range of approximately 0.125 inches to 0.150 inches. Again, other dimensional characteristics can be employed with various embodiments without deviating from the spirit and scope of the present invention. FIGS. 4-4b depict an embodiment having a single flat portion 16 and a larger single curved portion 18, e.g., 0.175 inch to 0.200 inch diameter D. FIGS. 3-3b show an embodiment having two opposing flat portions 16 and two opposing curved portions 18. The flat portions 16 can be approximately 0.125 inches to 0.140 inches in length, with the vertical dimension B ranging approximately between 0.120 inches and 0.140 inches. Again, other dimensional characteristics, proportions and shapes are envisioned for various embodiments.

Figure 6:
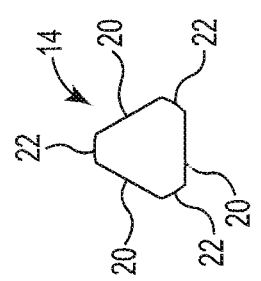
FIG. 6 is a schematic cross-sectional view of the non-circular trilobe needle device of FIG. 5, in accordance with embodiments of the present invention.

FIGS. 5-6 show an embodiment of the needle 14 having a generally trilobe configuration or cross-section. The trilobe configuration can be defined by three primary linear portions 20. In certain embodiments, the linear portions 20 are in direct communication to define a generally triangular shape. In other embodiments, as shown in FIG. 6, one or more secondary portions 22 extend between the linear portions 20. The secondary portions 22 can be generally linear or curved. For those embodiments having generally curved portions 22 the diameter D measurement for one or more of the portions 22 can range from approximately 0.175 inches to 0.190 inches. Again, other dimensional characteristics are envisioned for use as well. These various trilobe embodiments can provide a desirable tactile feedback and control structure for the needle 14 as well.

Other triangular, rectangular, octagonal, hectagonal, pentagonal, and like shapes and constructs, including other polygon shapes, can be implemented to achieve one or more non-circular needle 14 cross-sections to facilitate the objectives and advantages described herein.

Figure 7:
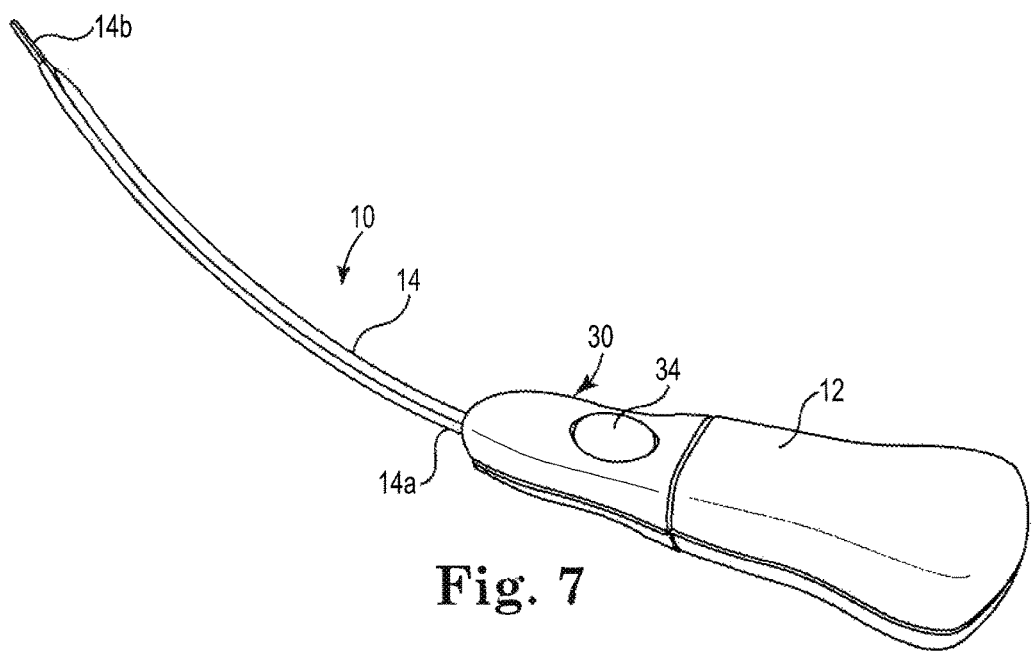
FIG. 7 is a schematic view of a needle device having a needle shaft, handle and slidable grip element, in accordance with embodiments of the present invention.
Figure 8:
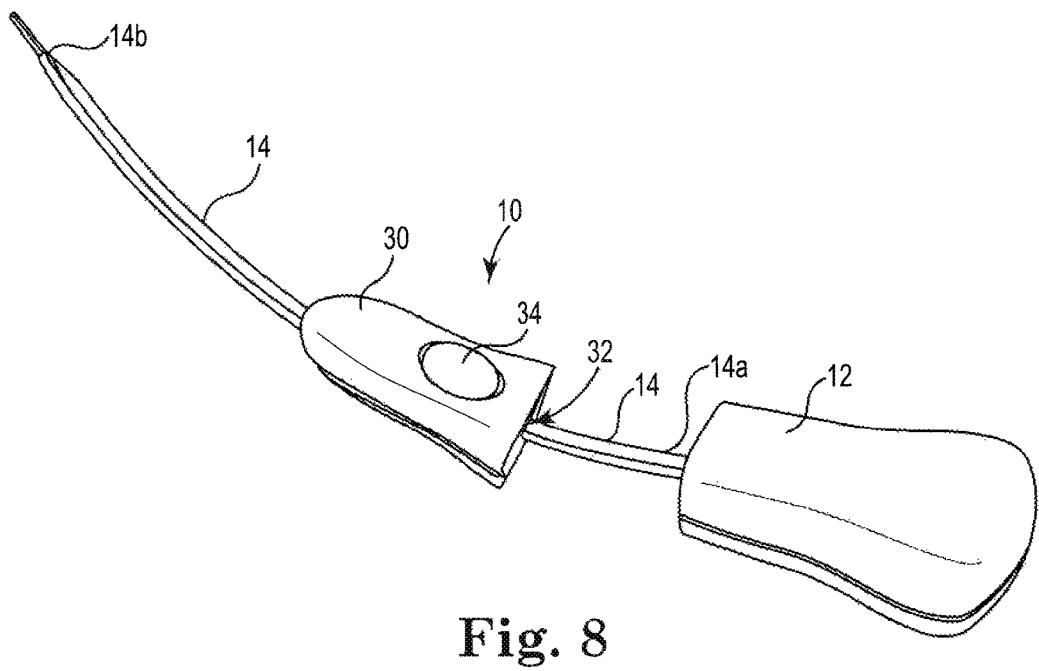
FIG. 8 is a schematic view of a needle device having a needle shaft, handle and slidable grip element slid a distance along a length of the shaft, in accordance with embodiments of the present invention.

FIGS. 7-8 show and describe various exemplary use applications for the needle device 10 having a housing or grip element 30. Again, the needle 14 can be connected to the handle 12. In certain embodiments, the grip 30 is constructed of a rigid plastic material, suitably shaped for gripping by the physician's fingers and/or hand. The outer portions of the grip 30 can include various surface textures or features to further facilitate handling and gripping.

The grip element 30 can include flats, curved portions, holes, a through-aperture 32 or other constraining means by which it may be slidably attached to the needle 14. In certain embodiments, for instance, the through-aperture 32 is shaped and sized to generally match the shape and size of the needle 14 (except it can be measurably larger to permit sliding along the needle 14), e.g., non-circular cross-section. As such, the grip element 30 can slide along a longitudinal length of the non-circular cross-section needle 14, while still restricting rotational movement about the needle shaft. A mechanism 34 can be included with the housing 30, e.g., button or actuator, to selectively stop sliding of the element 30 along the needle 14 when desired. The mechanism 34 can be a stop member, ratchet mechanism, a friction feature or element or like mechanism operatively connected with the mechanism 34. Such a mechanism 34 can be in operative communication with a rubber member or element adapted for selective engagement with the needle shaft. The mechanism 34 allows the physician to apply both axial and rotational loads on the needle 14 during implant introduction or deployment.

In certain embodiments, the grip element 30 can be employed with a needle 14 having a generally circular cross-section. Further, various embodiments of the mechanism 34 can be initially biased or engaged with the needle to restrict sliding of the grip 30 along the needle 14 until the mechanism 34 is actuated or released.

To use the device 10, a physician or end user actuates or releases the mechanism 34 to permit slidable repositioning of the element 30 along the needle 14. When at the desired position, the stop mechanism 34 is re-engaged, or released, to allow the physician to apply both axial and rotation loads to the needle 14. This element 30 can be particularly useful with "top-down" or like retropubic needle passes in which the physician commonly manipulates the needle 14 directly rather than via the handle 12.

Alternatively, the element 30 can serve as a bearing surface particularly useful when passing a needle through the anatomical structure during a "bottom-up" implantation procedure. With the mechanism 34 disengaged, the device 10 may be held in one hand while the other hand is free to push the needle from the handle. With curved needles 14, this allows the needle to advance along its curved shape without pushing into or dragging along the hand holding the needle.

Figure 9:
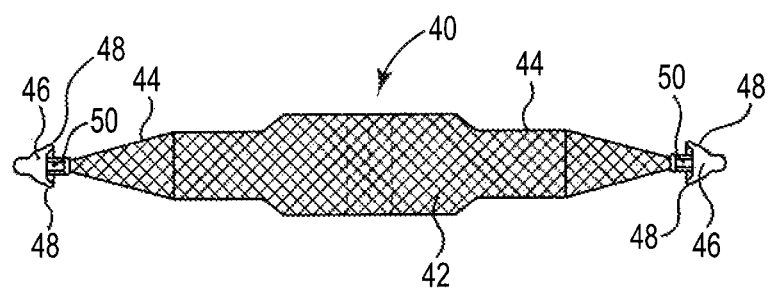
FIGS. 9-10 are schematic views of pelvic implant devices for use with needle devices, in accordance with embodiments of the present invention.
Figure 10:
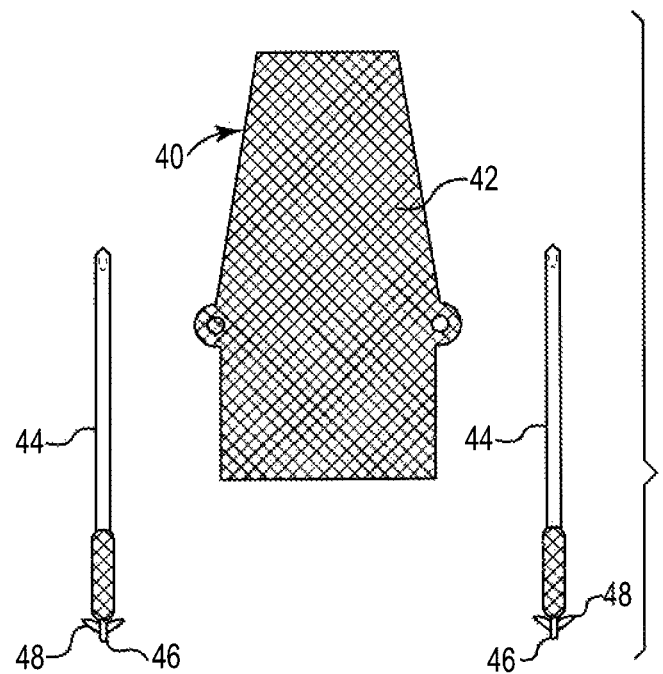

As shown in FIGS. 9-10, various embodiments of implantable sling or mesh devices 40 and methods adapted to include certain anchoring and other implant structures or devices are disclosed herein for use with the present invention. In general, the implant devices 40 can include a support portion 42, and extension or arm portions 44 having anchors 46 provided therewith. Various anchor 46 embodiments provided herein can include one or more extending tines or barbs 48 to promote tissue engagement and fixation. An aperture or other engagement portion 50 can be included with the device 40, e.g., the anchors 46, and adapted to selectively or releasably engage with the device 10, e.g., the needle tip 14b. Various portions of the implant device 40 can be constructed of polymer materials from a mesh of filaments. Certain embodiments can be constructed of or from a film or sheet material of polypropylene, polyethylene, fluoropolymers or like compatible materials.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2012/0157761, 2011/0144417, 2011/0124956, 2010/0105979, 2002/151762 and 2002/147382. Accordingly, the above-identified disclosures are fully incorporated herein by reference in their entirety.

The implant systems, tools, devices, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the systems, devices, device portions, components or structures disclosed herein can be constructed of compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An implant introduction system, comprising:
an implant introduction device, including;
a handle portion having a proximal portion and a distal portion, and a first side and a second side in which a distance between the first side and the second side defines a width;
a needle having a distal tip portion, a shaft portion, and a proximal portion operatively connected to the distal portion of the handle portion, the distal tip portion having a cross-sectional shape that is smaller than a cross-sectional shape of the shaft portion;
wherein the shaft portion has a non-circular cross-section;
an elongate grip device having a proximal end and a distal end defining a grip length, and a first side and a second side in which a distance between the first side and the second side defines a width, the width of the grip device being smaller than the width of the handle portion, the grip device configured to slide along a length of the shaft portion of the needle relative to the handle portion such that the proximal end of the grip device is slidable away from and abuttable with the handle portion, the grip device having a side gripping feature, and a manual actuation mechanism recessed within the grip device, provided substantially flush with an outer surface of the grip device, and adapted to selectively limit sliding of the grip device along the shaft portion; and
an implant device including a mesh implant having a first end portion and a second end portion, the implant device including an anchor coupled to the first end portion of the mesh implant, the anchor including a distal end portion having one or more barbs configured to engage with tissue, the anchor including proximal end portion defining an aperture, the aperture of the proximal end portion of the anchor configured to selectively receive the distal tip portion of the needle.

2. The system of claim 1, wherein the non-circular cross-section of the shaft portion is generally elliptical.

3. The system of claim 1, wherein the non-circular cross-section of the shaft portion includes one or more flat portions.

4. The system of claim 3, wherein the non-circular cross-section of the shaft portion includes one or more curved portions.

5. The system of claim 1, wherein the non-circular cross-section of the shaft portion defines a trilobe cross-section.

6. The system of claim 1, wherein the cross-sectional shape of the distal tip portion is different than the cross-sectional shape of the shaft portion.

7. The system of claim 1, wherein the shaft portion is a curved shaft, the curved shaft having a first side and a second side opposite to the first side, the first side being flat, the second side being curved.

8. The system of claim 1, wherein at least the shaft portion of the needle is constructed of metal.

9. The system of claim 1, wherein at least a length of the shaft portion of the needle is curved.

10. The system of claim 1, wherein the shaft portion has a curve defining a bend, the curved shaft having a first side extending a majority of a length of the needle, and a second side extending a majority of a length of the needle, the second side being opposite to the first side, the first side being flat and facing towards an inside of the bend, the second side being curved and facing toward an outside of the bend.

11. A needle introduction device, comprising:
a fixed handle portion having a proximal portion and a distal portion, and a first side and a second side in which a distance between the first side and the second side defines a width;
a needle having a distal tip portion, a shaft portion, and a proximal portion operatively connected to the distal portion of the handle portion, the shaft portion having a non-circular cross-section, the distal tip portion having a cross-sectional shape that is smaller than a cross-sectional shape of the shaft portion;
an elongate grip portion having a distal portion, a proximal portion, a first side, and a second side, in which a distance between the first side and the second side defines a width, the width of the grip portion being smaller than the width of the handle portion, the grip portion configured to slide along a length of the shaft portion such that the proximal portion is abuttable against the fixed handle portion, the grip portion having a side gripping feature, and a generally flush button mechanism, recessed within the grip portion, and adapted to selectively limit sliding of the grip portion along the shaft portion; and
an implant device including a mesh implant having a first end portion and a second end portion, the implant device including an anchor coupled to the first end portion of the mesh implant, the anchor including a distal end portion having one or more barbs configured to engage with tissue, the anchor including proximal end portion defining an aperture, the aperture of the proximal end portion of the anchor configured to selectively receive the distal tip portion of the needle.

12. The device of claim 11, wherein the non-circular cross-section of the shaft portion is generally elliptical.

13. The device of claim 11, wherein the non-circular cross-section of the shaft portion includes one or more flat portions.

14. The device of claim 13, wherein the non-circular cross-section of the shaft portion includes one or more curved portions.

15. The device of claim 11, wherein the non-circular cross-section of the shaft portion defines a trilobe cross-section.

16. The device of claim 11, wherein the handle has a handle abutment portion having a peripheral edge, and the grip portion has a grip abutment portion having a peripheral edge substantially matching a size and shape of the peripheral edge of the handle abutment portion.

17. The device of claim 16, wherein the shaft portion is a curved shaft, the curved shaft having a first side and a second side opposite to the first side, the first side being flat, the second side being curved.

18. The device of claim 11, wherein the grip portion includes a non-circular through-aperture adapted to substantially match the non-circular cross-section of the shaft portion.

19. The device of claim 11, wherein at least a length of the shaft portion of the needle is curved.

20. A needle introduction device, comprising:
a fixed handle portion having a proximal portion and a distal portion;
a needle having a distal tip portion, a shaft portion, and a proximal portion operatively connected to the distal portion of the handle portion, the shaft portion having a non-circular cross-section, the distal tip portion having a cross-sectional shape that is smaller than a cross-sectional shape of the shaft portion,
wherein the shaft portion has a curve defining a bend, the curved shaft having a first side extending a majority of a length of the needle, and a second side extending a majority of a length of the needle, the second side being opposite to the first side, the first side being flat and facing towards an inside of the bend, the second side being curved and facing toward an outside of the bend;
an elongate grip portion having a distal portion, a proximal portion, and adapted to slide along a length of the shaft portion such that the proximal portion is abuttable against the fixed handle portion, the grip portion having a side gripping feature, and a generally flush button mechanism, recessed within the grip portion, and adapted to selectively limit sliding of the grip portion along the shaft portion; and
an implant device including a mesh implant having a first end portion and a second end portion, the implant device including an anchor coupled to the first end portion of the mesh implant, the anchor including a distal end portion having one or more barbs configured to engage with tissue, the anchor including proximal end portion defining an aperture, the aperture of the proximal end portion of the anchor configured to selectively receive the distal tip portion of the needle.

* * * * *